United States Patent [19]

Michelson

[11] 4,029,819

[45] June 14, 1977

[54] SUPEROXIDE DISMUTASE AND ITS APPLICATION AS AN OXIDATION INHIBITOR

[75] Inventor: Adolf Michael Michelson, Chatenay-Malabry, France

[73] Assignee: Etablissement Public det: Agence Nationale de Valorisation de la Recherche Anver, Paris, France

[22] Filed: Aug. 22, 1976

[21] Appl. No.: 713,670

Related U.S. Application Data

[60] Division of Ser. No. 575,025, May 6, 1975, Pat. No. 3,997,402, which is a continuation-in-part of Ser. No. 461,379, April 16, 1974, abandoned.

[30] Foreign Application Priority Data

Apr. 16, 1973 France .............................. 73.13670

[52] U.S. Cl. .................................. 426/61; 426/7; 195/63; 195/126
[51] Int. Cl.² .......................................... A23L 3/34
[58] Field of Search ............... 195/126, 63; 426/61, 426/7

[56] References Cited

UNITED STATES PATENTS 3,920,521  11/1975  Michelson et al. .............. 426/61 X

*Primary Examiner*—Lionel M. Shapiro
*Attorney, Agent, or Firm*—Hammond & Littell

[57] ABSTRACT

The invention relates to a process for the production of superoxide dismutase and the superoxide dismutase so obtained. The superoxide dismutase obtained is extracted from marine bacterial strains and is characterized in that it comprises non-hematinic iron or copper and zinc, it has a molecular weight of about 33,000 to 40,000 ± 2500 and a pHi or isoelectric point of about 4 to 8.2 and it has maximum enzyme activity at a pH of about 8.5 to 10 with an optimum at about 9 to 9.5 and the use of said superoxide dismutases for the protection of oxidizable systems from auto-oxidation.

6 Claims, No Drawings

SUPEROXIDE DISMUTASE AND ITS APPLICATION AS AN OXIDATION INHIBITOR

PRIOR APPLICATION

This application is a divisional application of my copending, commonly assigned U.S. patent application Ser. No. 575,025 filed May 6, 1975 now U.S. Pat. No. 3,997,402 issued Dec. 14, 1976, which is a continuation-in-part of my copending, commonly assigned U.S. application Ser. No. 461,379 filed Apr. 16, 1974, now abandoned.

OBJECTS OF THE INVENTION

It is an object of the invention to provide novel superoxide dismutase and to provide a novel process for its preparation.

It is a further object of the invention to provide a novel method of protecting oxidizable systems from auto-oxidation.

These and other objects and advantages will become obvious from the following detailed description.

THE INVENTION

This invention relates to the production of superoxide dismutase and particularly to a process for the production of a new superoxide dismutase enzyme containing iron.

Superoxide dismutases have already been described; these were extracted from bovine erythrocytes (Markovitz, J. Biol. Chem. 234, p. 40, (1959)) and from Escherichia coli (Keele and Fridovich, J. Biol. Chem. 245, p. 6176, (1970)). Superoxide dismutases are enzymes capable of inducing dismutation of superoxide ions according to the reaction:

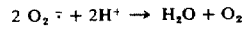

$$2 O_2^- + 2H^+ \rightarrow H_2O + O_2$$

They therefore contribute to providing a self-protection system for articles or organisms in which they are found, as the $O_2^-$ ions which are produced during oxidation reactions in response to molecular oxygen are very active and attack among others things, proteins, by oxidation of tryptophane among other amino acids and nucleic acids.

One object of this invention is a process for the production of superoxide dismutase extracted from marine bacterial strains and the superoxide dismutases so obtained, and preferably relates to a process for the extraction of superoxide dismutases from strains of Photobacterium phosphoreum, Photobacterium leiognathi and Photobacterium sepia among others.

The process according to the invention comprises dispersing a marine bacterial culture in water and maintaining it at about 4° C, centrifuging the culture and then adjusting the pH of the supernatant liquid to a pH of 6.5 – 8, preferably about 7, heating the mixture to 50° – 60° C for a few minutes, cooling it to about 4° C and, at this temperature, centrifuging it, effecting a first fractional precipitation of the supernatant fraction by means of neutral salts, further centrifuging the mixture and effecting a second fractional precipitation of the supernatant fraction with neutral salts and centrifuging.

According to another embodiment of the process of this invention, there is provided a purification step consisting advantageously in dissolving the precipitate obtained in the last centrifugation in a pH 7.8 phosphate buffer and dialyzing the solution so obtained with the same pH 7.8 phosphate buffer to recover the superoxide dismutase as the inner dialysate.

According to still another embodiment of the process of the invention, the enzyme extracted from the marine bacterial culture is purified after mixing the product of the last centrifugation with pH 7.8 phosphate buffer and dialyzing against said same buffer, by chromatography which is preferably column chromatography and preferably chromatography on three successive columns which are respectively: a first Sephadex G 200 gel column, a diethylaminoethyl Sephadex column ((DEAE-Sephadex A-50) and a second Sephadex G 200 gel column.

The bacterial culture used as the enzyme source in the process of the invention is, for example, a culture of strains of Photobacterium phosphoreum, Photobacterium leiognathi or Photobacterium sepia. To adjust the pH of the dispersion of bacteria in water to a pH of 6.5 – 8 which is the first step of said process, 2N ammonium hydroxide solutions are used, and for example, the lysate is centrifuged and potassium chloride, preferably 3M KCl, is then added to a final concentration of 0.1 M.

The mixture so formed is heated to a temperature of 50° to 60° C, for a few minutes only, and preferably for 3 to 4 minutes. The mixture is then cooled to about 4° C, all the following steps of the process of the invention being effected at this temperature. Each of the fractional precipitations constituting the steps of said process is realized, as indicated above, by means of neutral salts in aqueous solution and preferably with ammonium sulfate.

According to an advantageous embodiment of the process of the invention, the first fractional precipitation is carried out with ammonium sulfate added in an amount so that the final concentration in the enzyme mixture or extract so treated is about 30 to 35% of saturation at 4° C. It should, however, be noted that all, or a portion, of the ammonium sulfate can be replaced by one or more other suitable salts and the total amount of said salts is then an equivalent and suitable amount to provide a final concentration of about 30 to 35% of saturation at 4° C.

According to a further embodiment of the process of this invention, an ultrafiltration system can be used such as, for example, a system in which a porous device such as porous tubes is used, and preferably a system using a first porous tube retaining, and concentrating, the molecules having a molecular weight higher than 40,000 and a second porous tube through which the enzyme molecules desired can pass but which retains the remaining debris and bacteria thus providing a sterile enzyme extract.

Similarly, the second fractional precipitation is advantageously realized with ammonium sulfate added in an amount so that the final concentration in the enzyme mixture or extract treated is about 70 to 75% of saturation at 4° C.

The superoxide dismutases obtained from various marine bacterial strains by the process of the invention are all superoxide dismutases comprising non-hematinic iron, while the enzymes having a superoxide dismutase activity which have been previously described and which are erythrocupreine and the enzyme extracted from Escherichia coli comprise divalent cations which are, respectively, copper and zinc for the first and manganese for the second.

The presence of a metal in the superoxide dismutases in question can be detected by atomic absorption spectrography analysis and corresponds to 1 to 2 atoms of iron per molecule of enzyme.

A colorimetric test can also be carried out which, in the present case, consists in staining an electrophoretic migration gel of a preparation of the enzyme with a specific stain for ferrous iron $Fe^{2+}$, bathophenanthroline, optionally in the presence of a reducing agent such as hydrazine. For this test, the gel is cut in half lengthwise and one of the two portions is placed in coomassie blue and other portion in bathophenanthroline. The test is positive if, in the latter case, a pink ring is obtained at the level of the protein band. Now, as is known, the appearance of such a pink ring can be considered as being an indication of the presence of ferrous iron in the superoxide dismutase protein. The use of radioactive iron can be envisaged for marking the protein and determine the stoechiometric amount of it with respect to the divalent metal cation present.

Another object of the present invention is, therefore, a superoxide dismutase extracted from marine bacterial cultures and characterized in that it comprises non-hematinic iron, it has a molecular weight of about 40,000 ± 2500 and a pHi or isoelectric point of about 4 to 7 and has maximum enzyme activity with a pH of about 8.5 to 10, with an optimum at about pH 9.5, but is active between pH 4.5 and 10.5. The enzyme can be maintained active over a long period of time by preserving it in a 70 – 80% solution of neutral ammonium sulfate at 4° C.

A further object of the invention is a superoxide dismutase extracted from marine bacterial cultures, which contains 1 atom of copper and 2.0 atoms of zinc per mole of superoxide dismutase, has a molecular weight of 33,000 ± 2500, a pHi point of 8.25 and a maximum enzymatic activity at a pH of about 8.5 to 10.

To measure the activity of the superoxide dismutases produced according to the invention, it is possible to assess the inhibition by the latter of the chemiluminescent reaction induced by the oxygen/hypoxanthine/xanthine oxidase/luminol system as will be shown further on. Said reacting enzymatic system induces the release of $O_2^-$ ions which are able to give a chemiluminescence reaction with luminol. The addition of superoxide dismutase to said system in fact diverts $O_2^-$ ions and thus induces a decrease in the intensity of light emitted in said reaction.

The superoxide dismutases catalyse the reaction:

$$2 O_2^- + 2 H^+ \rightarrow H_2O_2 + O_2$$

If the superoxide ions produced by the enzyme reaction using xanthine-oxidase and xanthine or hypoxanthine are used as substrates in said reaction, the superoxide ions thus produced are very unstable and emit light spontaneously. The latter is, however, too weak and the measurements are not sufficiently reproducible. This is why, in practice, the analytic device is completed by using, to demonstrate the amount of superoxide ions formed, a chemioluminescent substance, luminol or 5-amino-2,3-dihydro-1,4-phtalazine-dione.

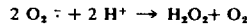

Luminol + $O_2^-$ → H ν+ oxidation product.

The applicant has, moreover, also developed superoxide ion producing systems, catalytic systems able to induce the oxidation of luminol consisting of $Fe^{2+}$, $Ni^{2+}$ or $Co^{2+}$ ions in aqueous solutions of molecular oxygen in the presence of certain ligands. The superoxide dismutase introduced into the system decreases the amount of $O_2^-$ ions and, consequently, the production of light.

Determination is effected as follows in which the following reaction mixture is used:

| | | |
|---|---|---|
| Luminol | $10^{-3}$M | 0.3 ml |
| Phosphate buffer | $10^{-3}$M pH 7.8 | 0.3 ml |
| EDTA | $10^{-3}$M | 0.3 ml |
| Water qs | | 2 ml |

+ 50 μg xanthine oxidase (0.05 ml of a 1 mg/ml solution of xanthine-oxidase).

The said mixture is placed in a silver-lined cuvette in front of a photomultiplier. The reaction is initiated by injecting into the cuvette the substrate: 1 ml of a solution containing 0.3 μmole hypoxanthine.

A photon flux is then emitted which, in response to the photomultiplier, gives rise to a current the intensity of which is measured by a picoamperemeter and recorded. If 5 μl of the superoxide dismutase to be determined is introduced into the reaction mixture prior to initiation of the reaction, said emission of light is inhibited. The unit of superoxide dismutase enzymes is then defined arbitrarily as being the amount of said enzyme which induces a 50% inhibition of said light emission.

It should, however, be noted that it is also possible to determine the activity of the superoxide dismutases of the invention by inducing inhibition of the same reaction as the mentioned hereabove, directly by injecting 1 ml of a solution of $O_2^-$ ions, prepared by electrochemical reduction (J. M. Cord, I. Fridovitch, J. B. C. vol. 244, 25 (1969) pp. 6049 – 6055), in 2 ml of a solution containing 0.5 μmole of luminol and 0.17 millimole of pH 7.8 phosphate buffer.

As a variant, the activity of the superoxide dismutases of the invention can be determined as follows: 0.3 ml of glycine —NaOH buffer 1M, pH 9, 0.3 ml of $10^{-3}$M neutralized EDTA, 1.1 ml of $10^{-5}$M flavine-mononucleotide and 0.3 ml of luminol (20 mg/ 70 ml) are introduced into the above-mentioned cuvette followed by injection of 1 ml of $10^{-2}$M of Na $BH_4$. Under these conditions, a signal determined as being $10^{-7}$ to $10^{-8}$ A for a voltage of 1500 V is obtained. It will be noted that the Na $BH_4$ solution should be freshly prepared whereas the luminol must be stored away from light at 0° C and should be added separately to the reaction mixture. The addition of superoxide dismutase to said system induces a certain inhibition of the light signal, the latter varying linearly with the amount of enzyme to a rate of 75%.

According to yet another variant, the activity of superoxide dismutases can be determined by using a reaction mixture composed of 0.3 ml of glycine-NaOH 1M pH 9 buffer, 0.3 ml of $10^{-3}$M EDTA, 1.1 ml of water and 0.3 ml of $10^{-4}$ M luminol. 5 μl of xanthine-oxidase (1 mg/ml) and an aliquot amount of superoxide dismutase is added to said mixture. 1 ml of hypoxanthine (3 × $10^{-5}$M) is injected. It should be noted that the luminol, which should be stored away from light and at 0° C, is to be added separately to the reaction mixture.

The signal obtained for determining the control (without superoxide dismutase) is about $10^{-7}$ A for a voltage of 1500 V and inhibition of the light signal is linear and proportional to the amount of superoxide dismutase to 50%.

Having assumed that, under suitable conditions, $Fe^+$, $Ni^{2+}$ and $Co^{2+}$ metal ions can provide superoxide radicals, the applicant studied the problem of the oxidation of lipids, preferably in foodstuffs containing them, and compared it to the reaction mechanism of that of the formation of superoxide ions by a system comprising the aforesaid metal ions and a suitable ligand. It was then established that the antioxidants usually used in the foodstuff industry, such as free radical chain interupters of the pyrogallol type, such as propyl gallate, or free radical production inhibitors such as EDTA and ascorbic acid can, in fact, and contrary to all expectations, encourage certain oxidations catalyzed either with enzymes or in response to metal ions, instead of acting as antioxidants as was expected.

It was then established that, under suitable conditions of pH, the superoxide dismutases of the present invention inhibit oxidizing systems such as those consisting of $O_2^-$ ions produced electrochemically, by $FMNH_2/O_2$, or $Fe^{2+}$, $Ni^{2+}$ or $CO^{2+}$ ions in aqueous solutions of molecular oxygen in the presence of suitable ligands. Thus, 7 units of superoxide dismutase extracted from *Photobacterium leiognathi* were found to inhibit to 16.5% the emission of light due to the action of the $Co^{2+}/O_2$ tetraglycine system on luminol at pH 9.7, and to about 40% that due to the action of the $Ni^{2+}/O_2$ cyanide system on luminol at pH 9.

It was demonstrated that superoxide dismutases effectively protect lipids and the antioxidants and other preservations usually used in the foodstuff industry by very strongly inhibiting the reactions connected with the production of the superoxide $O_2^-$ ion. It was notably established that the auto-oxidation of unsaturated lipids obtained from Anchoveta is very strongly inhibited by superoxide dismutases. Furthermore, other trials demonstrated that superoxide dismutases have a protective action with respect to the auto-oxidation of certain anti-oxidants, notably the anti-oxidants used for preserving foodstuffs, such as pyrogallol or ascorbic acid.

The invention is further illustrated by the following examples, which are illustrative of this invention rather than restrictive of its scope.

EXAMPLE 1

*Photobacterium leiognathi* bacteria, strain n ATCC 25 521 were cultured on a synthetic medium containing, in grams per liter

| NaCl | 30 g/l |
|---|---|
| $Na_2HPO_4, 12H_2O$ | 18.7 |
| $KH_2PO_4$ | 2 |
| $MgSO_4, 7H_2O$ | 0.2 |
| $(NH_4)_2HPO_4$ | 0.5 |
| Glucose | 1.5 |
| Glycerol | 1.5 |
| Trypticase | 5 |
| Yeast extract | 5 |

This medium was adjusted to pH 7.2 with sodium hydroxide and was sterilized for 1 hour at 110° C. 1 liter of preculture was used, grown overnight and divided into 4 Erlenmeyer flasks each containing 250 ml of the medium to seed a fermenter of 12 liters of medium. Culturing was carried out for 12 hours at 20° C with strong ventilation and 100 g of bacteria, expressed at moist weight of product, were thus obtained.

135 g by moist weight of *Photobacterium leiognathi* bacteria from several cultures were dispersed in 650 ml water and left to stand for one night at 4° C. 2N ammonium hydroxide solution was added to obtain a medium with a pH of 7 – 8, and then 18 ml of 3M KCl were added. The mixture was heated to 58° C and maintained at this temperature for 4 minutes and then cooled to 4° C and centrifuged for 10 minutes at a velocity of 10,000 revolutions minute. Still operating at 4° C, the supernatents were adjusted to 35% saturation with solid ammonium sulfate at pH 8. After centrifugation, the supernatant was adjusted to 75% of ammonium sulfate saturation and was left to stand overnight at 4° C. The precipitated protein was recovered by centrifugation and preserved in a 75% ammonium sulfate solution.

The activity of a solution of 9 mg of protein per milliliter (Biuret) was 40 units/mg, whereas it was, by comparison, 0 unit/mg for catalyse in solution at 9 mg protein/ml. After a further fractional precipitation with ammonium sulfate with a concentration gradient of 35 to 75% saturation, a superoxide dismutase was obtained which, in a solution of 14.8 mg of protein/ml (Biuret) had an activity of 134 units/mg to 500 units/mg. The protein precipitate was dissolved in a pH 7.8 phosphate buffer and dialyzed for 48 hours at 4° C and the superoxide dismutase enzyme was kept at $-20°$ C.

To determine the activity of the latter product, a cuvette containing the following reaction mixture:

| Luminol | $10^{-3}M$ | 0.3 ml |
|---|---|---|
| Phosphate buffer | $10^{-3}M$ pH 7.8 | 0.3 ml |
| EDTA | $10^{-3}M$ | 0.3 ml |
| Water | | 1.0 ml |
| Xanthine oxidase | (1 mg/ml) | 0.050 ml | was placed in front of a photomultiplier. The reaction was initiated by injecting into the cuvette 1 ml of 3 × $10^{-4}M$ by hypoxanthine. A photon flux was then emitted which, in response to the photomultiplier, gave rise to a current, the intensity of which was measured with a picoamperemeter, with the variations in said intensity also being recorded.

By introducing 5 μl of a superoxide dismutase solution, prepared as described above, into the reaction mixture before initiation of the reaction, inhibition of light emission was obtained and it was assumed arbitrarily that 1 unit of superoxide dismutase enzyme could be the amount of enzyme which induces 50% inhibition of light emission. With UV spectroscopy, the superoxide dismutase extract gave the conventional spctra of non-hematinic proteins with absorption due to tryptophane at 290 mμ.

Two known techniques were used to determine the molecular weight; one consisting in determining a centrifugation gradient with sucrose and the other using a Sephadex G 200 gel. The following tracers, the molecular weights (M.W.) of which are known, were used for this purpose:

| | M.W. |
|---|---|
| Yeast alcohol dehydrogenase | 150,000 |
| Bovine albumine | 66,000 |
| Peroxidase | 40,000 |

A molecular weight of 40,000 ± 2500 were observed. Electrophoresis in polyacrylamide gel with added 10% SDS (sodium dodecyl sulfate) was used to determine the subunits of the protein structure of the enzyme. Only one type of sub-unit was observed with a molecular weight of about 21,000. The molecular weight of the superoxide dismutase obtained can therefore be estimated at 21,000 × 2 or 42,000. Still using the polyacrylamide gel, a red band was obtained in the presence of bathophenanthroline and hydrazine precisely at the level of the band of superoxide dismutase revealed by coomassie blue.

A protein solution was subjected to colorimetric determination and, for iron, a value was obtained which, estimating the molecular weight of the enzyme at 42,000, gave about 2 iron atoms per mole. Atomic absorption spectrometry of a 0.2 mg/ml of protein solution confirmed this figure. The number of iron atoms per mole of superoxide dismutase can therefore reasonably be assumed to be 1 to 2.

Furthermore, the enzyme extracted according to this example was found not to undergo an appreciable loss of activity after 5 minutes at a temperature of 70° C. Electrofocalization of the superoxide dismutase enabled the pHi or isoelectric point of said enzyme to be assessed as 4.4. The enzyme had maximum activity for a pH of about 9.5 but was active between pH 4.5 and 10.5.

A similar enzyme, with similar characteristics, was obtained from a bacterial strain of *Photobacterium sepia* bacteria, strain no. ATCC 15,709. This enzyme was nevertheless immunochemically distinct from that isolated from *Photobacterium leiognathi*.

EXAMPLE 2

A culture of *Photobacterium sepia* bacteria of strain no. ATCC 15,709 was subjected to lysis by stirring it in cold water, at a rate of 1 g of moist weight of bacteria for 4 ml of water. It was then centrifuged at 16,000 revolutions minute for 20 minutes at 4° C. 3M KCl was added to the pale yellow supernatant until a final concentration of 0.1M was obtained. The solution was heated for 3 to 4 minutes in a water bath at 55° C and it was then cooled to 4° C and clarified by centrifugation.

The supernatant was subjected to fractional precipitation by the addition of solid ammonium sulfate. The active fraction precipitated at between 45 and 74% ammonium sulfate saturation and was separated out by centrifugation. It was redissolved in the minimal volume of $4 \times 10^{-3}$M, pH 7.8 $K_2HPO_4$ and dialyzed for one night using the same phosphate buffer. The inner product of said dialysis was then added to a Sephadex G 100 or G 200 column, equilibrated with $5 \times 10^{-3}$M, pH 7.8 phosphate buffer. The active fraction eluted was concentrated with an ultracentriguation membrane Diaflo PM-10, and was then dialyzed for one night with $5 \times 10^{-3}$M, pH 7.8 $K_2HPO_4$.

The superoxide dismutase enzyme was adsorbed on a DEAE-Sephadex A-50 column buffered with $5 \times 10^{-3}$M, pH 7.8 $K_2HPO_4$. The protein was eluted from the column with a linear gradient of pH 7.8 (from $5 \times 10^{-3}$M to $3 \times 10^{-1}$M) $K_2HPO_4$. The superoxide dismutase was thus eluted with $1.4 \times 10^{-1}$M phosphate and was then concentrated A further filtration was effected under the same conditions as the previous one on a DEAE-Sephadex A-50 column. The enzyme was thus eluted at a phosphate concentration of $1.6 \times 10^{-1}$M and was concentrated.

The protein so extracted and purified gave a single band when subjected to electrophoresis on acrylamide gel (100 μg of protein for a gel). 3 mg of pure superoxide dismutase were thus obtained from 20 g of frozen *Photobacterium sepia* cells (with a superoxide dismutase activity of 5000 units/mg). The enzyme was maintaned active over a long period of time by preserving it in a 70 to 80% solution of $(NH_4)_2SO_4$ at 4° C.

The molecular weight of the purified enzyme was determined by ultracentrifugation at 40,000 revolutions minute for 16 hours at 4° C. The sedimentation rate was determined by the Martin and Ames method with a linear sucrose gradient of 5 to 20 (by weight volume) and using a Beckman Spinco, model L2-65B, apparatus, with a SW65K rotor. A sedimentation coefficient of 3.2 was obtained with this dismutase, compared with a coefficient of respectively 4.82 and 7.4 for alcohol deshydrogenases of horse liver and yeast. From said constant of sedimentation, the molecular weight of the superoxide dismutase mutase extracted with therefore calculated as being about 42,500. It was also established that the molecule of said protein contained 1 to 2 iron atoms.

Electrophoresis with acrylamide gels gave, for the dismutase, a single band corresponding to a molecular weight of 20,000 to 20,500, thus demonstrating that the protein molecule was composed of two identical sub-units. The superoxide dismutase was also shown to be very resistant to the proteolytic action of trypsin as 150 μg of said superoxide dismutase treated with 10 μg of trypsine at 20° C for 60 minutes resulted in no change in enzyme activity or in the electrophoretic mobility of the undissociated protein.

The enzyme obtained was very stable with respect to heat: no less of enzymatic activity was observed after 30 minutes at 20° C, 30° C or even 40° C; 28% decrease in activity was observed after 15 minutes at 50° C; loss of activity was only 50% after 30 minutes at 50° C and only 10% and 50% after, respectively, 3 minutes and 10 minutes at 60° C. Electrofocalization of the superoxide dismutase enabled the pHi or isoelectric point of said enzyme to be determined as 4.1. Using a solution of $O_2^-$ ions prepared by the electrolytic method, the enzyme was found to have maximum activity at a pH of 8.5 to 10, with an optimum at pH 9.5.

EXAMPLE 3

A strain no. ATCC 11,040 of *Photobacterium phosphoreum* bacteria, which are marine bacteria and consequently have a high internal saline concentration, was used. Bacterial lysis was spontaneous in a $10^{-3}$M, pH 7.8 EDTA solution. Cellular debris was eliminated by centrifugation at 16,000 revolutions minute for 20 minutes and at 0° C. Preliminary studies had shown that the superoxide dismutase enzyme was stable at 50° C and therefore the other proteins, which are thermolabile, were eliminated by heating the lysate at 50° C for 3 minutes after addition of KCl to obtain a molarity of 0.1, and the denatured proteins were separated out by conventional centrifugation.

The operation was continued at 4° C. At said temperature, fractional precipitation was effected with ammonium sulfate added in an amount such that the enzyme mixture or extract treated had a concentration gradient of about 0 to 30% of saturation at 4° C. The precipitated fraction was eliminated by centrifuging for 45 minutes at 16,000 rotations minute and at 0° C. An amount of neutral ammonium sulfate necessary to bring it to 75% of saturation at 4° C was added to the supernatant. The precipitated fraction was recovered by a centrifugation similar to the preceding one and contained most of the superoxide dismutase.

In order to purify the superoxide dismutase so extracted, the precipitate collected was dissolved in a little $5 \times 10^{-3}M$, pH 7.8 phosphate buffer and was dialyzed against this same buffer for 48 hours at 4° C to obtain an extract (A). The proteins still present were then separated as a function of the size of their molecules using a Sephadex G 100 gel, the grain reticulation of which is such that it excludes proteins having a molecular weight higher than 100,000 which are thus very rapidly discharged to the outside of the gel. The molecules of lower molecular weight penetrate into the gel and are eluted from it more or less rapidly according to their size.

To effect this, the Sephadex resin was left to swell in water for 3 hours, was degassed and filtered on a Buchner funnel to remove the water and was then placed in the filtration buffer and poured into a 50 cm long, 3 cm inner diameter column. The column was equilibrated by flowing 2 liters of buffer therethrough. The enzyme extract (A) obtained by dialysis was first concentrated on a Diaflo millipore (P.M. -10) membrane with pressurized nitrogen to a volume of 5 ml. Said concentrate was deposited on the column prepared as described above and was eluted by flowing 500 ml of $5 \times 10^{-3}M$, pH 7.8 phosphate buffer. The flow rate was 1 drop every 8 seconds and 2.5 ml fractions were recovered. Those having a notable activity were combined and concentrated on a Diaflo membrane to obtain a concentration extract (B).

A further purification step was effected by chromatography on an ion exchange resin comprising DEAE Sephadex, a resin on which proteins are eluted according to their charge by buffers on increasing ionic strength. To prepare the column, the resin was put to swell in water and then degassed and washed in the following solutions: 0.5 M NaOH and 0.5 M $KH_2PO_4$ taking care to rinse the resin with distilled water between each step to an approximately neutral pH. After filtration on a Büchner funnel, the resin was put in suspension in 0.1 M pH 7.8 phosphate buffer and was placed in a 30 cm long, 3 cm inner diameter column. The column was equilibrated by flowing 300 ml of 0.1 M buffer.

The concentrated extract (B) was placed in the column so prepared. When this extract was completely absorbed, it was eluted with 500 ml of pH 7.8 phosphate buffer composed of 250 ml of 0.1 M phosphate buffer to which 250 ml of 0.5 M phosphate buffer was progressively added. The flow rate was 1 drop every 5 seconds and the volume of fractions collected was 2.5 ml. The active fractions were combined and precipitated with ammonium sulfate, then kept in this form at −18° to −20° C. The purity of the superoxide dismutase enzyme was verified by electrophoresis on polyacrylamide gel.

The molecular weight of the enzyme was determined by studying elution during filtration of Sephadex G 200 and use of the relation Log (MW) = f (elution volume) and known tracers made it possible to attribute a molecular weight of about 40,000 to the superoxide dismutase extract. Said molecular weight was also determined by sucrose gradient centrifugation: 5 to 20% sucrose gradients were poured into $5 \times 10^{-3}M$ pH 7.8 phosphate buffer, while progressively mixing 2.60 ml of the 20% solution with 225 ml of the 5% solution in a suitable device.

Various protein tracers of known molecular weight and superoxide dismutase were deposited on said sucrose gradients. Equilibrium was obtained by centrifugation at 45,000 rotations minute at 5° C for 22 hours. The bottoms of the tubes were then pierced and fractions of 10 drops were recovered, on which the enzymatic activities exhibited by the various tracers used were determined. After having drawn the line representing the variation of molecular weight as a function of the number of the elution fraction, the molecular weight of the superoxide dismutase extracted from *Photobacterium phosphoreum* was estimated at about 40,000, which confirmed the previous result.

To determine the molecular weight of the protein subunits, the protein and tracers, the molecular weight of whose sub-units were known, were subjected to electrophoretic migration on polyacrylamide gel in the presence of sodium dodecyl sulfate. Analysis of a graph demonstrated that a value of 20,000 could be attributed to the molecular weight of each sub-unit of the superoxide dismutase molecule. This last was found to be still very stable at 50° C and to have maximum enzymatic activity for a pH of about 9.5. The pHi or isoelectric point of said enzyme was estimated to be 4.2 following electrofocalization of the superoxide dismutase.

A colorimetric test such as that previously described made it possible to demonstrate the presence of ferrous iron in the protein, a pink ring appearing at the level of the proteic band in an electrophoretic migration gel to which bathophenanthroline had previously been added. It was estimated that there were approximately 2 iron atoms per molecule.

In another connection, inhibition of the auto-oxidation of certain compounds in response to superoxide dismutase (SOD) was determined by operating as follows.

EXAMPLE 4

A solution of $2.5 \times 10^{-2}M$, pH 7.7 phosphate buffer $K_2HPO_4$ .3 ml of said solution (A) was obtained. The increase in the optical density (OD) was measured at 440 m$\mu$ per minute for various systems and the percentage of inhibition was deduced for each of the following systems:

|  | Increase of OD at 440 m$\mu$/minute | Inhibition % |
|---|---|---|
| (A) | 0.031 | — |
| (A) + 25 units of Photobacterium leiognathi (crude) SOD | 0.029 | 6.5 |
| (A) + 250 units of Photobacterium leiognathi (crude) SOD | 0.004 | 87 |
| (A) + 4 $\mu$g catalase | 0.046 | — |

Said superoxide dismutase was therefore shown to have an exceptional inhibiting effect on the auto-oxidation of pyrogallol.

EXAMPLE 5

The same procedure was adopted as in Example 4, except that in respectively $5.0 \times 10^{-4}M$, $2 \times 10^{-4}M$ and $10^{-4}M$ pyrogallol was dissolved in the phosphate buffer. The solutions obtained were called (B), (C) and (D). The following results were obtained:

|  | Increase of OD at 440 mμ/minute (× 10) | Inhibition % |
| --- | --- | --- |
| $5 \times 10^{-4}$M pyrogallol (in $2.0 \times 10^{-2}$M, pH 7.7 buffer). | | |
| (B) | 0.175 | — |
| (B) + 5 units of Photobacterium leiognathi (crude) SOD | 0.070 | 60 |
| (B) + 10 units of Photobacterium leiognathi (crude) SOD | 0.043 | 75 |
| (B) + 50 units of Photobacterium leiognathi (crude) SOD | 0.004 | 98 |
| (B) + 200 units of Photobacterium leiognathi (crude) SOD | 0.001 | 99.5 |
| (B) + μg of catalase | 0.135 | — |
| - pyrogallol $2 \times 10^{-4}$M (id.) | | |
| (C) | 0.054 | — |
| (C) + 2.5 units of Photobacterium leiognathi (crude) SOD | 0.026 | 52 |
| (C) + 5 units of Photobacterium leiognathi (crude) SOD | 0.012 | 78 |
| (C) + 10 units of Photobacterium leiognathi (crude) SOD | 0.005 | 91 |
| - Pyrogallol $10^{-4}$M (id.) | | |
| (D) | 0.030 | — |
| (D) + 1 unit of Photobacterium leiognathi (crude) SOD | 0.013 | 57 |

EXAMPLE 6

$10^{-4}$M pyrogallol solutions were prepared respectively in $5 \times 10^{-2}$M pH 8.8 and $2 \times 10^{-2}$M pH 7.7 phosphate buffer $K_2HPO_4$ saturated with molecular oxygen. Said solutions (E) and (F) had a volume of 2.5 ml. The increase of optical density at 440 mμ per minute was measured and the percentage of inhibition was deduced:

|  | Increase of OD at 440 mμ/minute (× 10) | Inhibition % |
| --- | --- | --- |
| $5 \times 10^{-2}$M $K_2HPO_4$ pH 8.8 | | |
| (E) | 0.365 | — |
| (E) × 1 unit of Photobacterium leiognathi SOD | 0.275 | 25 |
| (E) + 5 units of Photobacterium leiognathi SOD | 0.183 | 50 |
| (E) + 10 units of Photobacterium leiognathi SOD | 0.063 | 83 |
| (E) + 20 units of Photobacterium leiognathi SOD | 0.018 | 95 |
| $2 \times 10^{-2}$M $K_2HPO_4$ pH 7.7 | | |
| (F) | 0.062 | — |
| (F) + 10 units of Photobacterium leiognathi SOD | 0.016 | 74 |

It will be noted that 1 unit of enzyme in 2.5 ml corresponds to $2 \times 10^{-9}$M enzyme.

EXAMPLE 7

A solution of $10^{-4}$M ascorbic acid was prepared in a $2 \times 10^{-2}$M pH phosphate buffer. The variation of the optical density (OD) was measured at 265 mμ per minute for each of the following systems:

|  | Variation of OD at 265 mμ/minute | Inhibition % |
| --- | --- | --- |
| Control | 0.016 | — |
| Control + 7.5 units of Photobacterium leiognathi (crude) SOD | 0.005 | 69 |
| Control + 10 units of Photobacterium leiognathi (crude) SOD | 0 | 100 |
| Control + 15 units of Photobacterium leiognathi (crude) SOD | 0 | 100 |
| Control + 20 units of Photobacterium leiognathi (crude) SOD | 0 | 100 |
| -continued |  |  |
| Variation of OD at 265 mμ/minute | Inhibition % |  |

EXAMPLE 8

The same procedure was used in Example 7 except that $10^{-4}$M ascorbic acid was dissolved in a $5 \times 10^{-2}$M, pH 8.8 phosphate buffer.

|  | Variation of OD at 265 mμ/minute | Inhibition % |
| --- | --- | --- |
| Control | 0.093 | — |
| Control + 1 unit of Photobacterium leiognathi (crude) SOD | 0.079 | 15 |
| Control + 10 units | 0.001 | 99 |

EXAMPLE 9

The action of superoxide dismutases on the oxidation of luminol catalyzed by metal ions was determined as follows:

|  | Imax (× $10^7$ quanta/s/ml) | Inhibition % |
| --- | --- | --- |
| - Oxidizing catalytic system: $CO^{2+}/O_2/NH_4OAc$/dihydroxyfumaric acid | | |
| - pH 9.0 control | 16.2 | — |
| " + 140 units of Photobacterium sepia SOD | 7.3 | 55 |
| - pH 9.8 control | 16.5 | — |
| " + 140 units of Photobacterium sepia SOD | 11.0 | |
| - Oxidizing catalytic system $Ni^{2+}/O_2/NH_4OAc$/dihydroxyfumaric acid | | |
| - pH 9.0 control | 4.7 | — |
| " + 140 units of Photobacterium sepia SOD | 0.88 | 81 |
| - pH 9.8 control | 240 | — |
| " + 140 units of photobacterium sepia SOD | 80 | 67 |

EXAMPLE 10

A 10% by weight per volume suspension of Anchoveta lipid was prepared in a 0.1 M, pH 8 phosphate buffer. Crude superoxide dismutase of *Photobacterium leiognathi* was added at rate of 0.01% by weight of enzyme based on the lipid (that is to say, 0.1 mg of crude enzyme per g of lipid). The consumption of oxygen by said system was measured in a Warburg apparatus comparing it each time with a lipidic control of the same composition, but not comprising the added superoxide dismutase. Measurements were effected over successive periods of time and the results obtained were expressed in the form of a percentage of oxidation inhibition compared with the control which did not comprise added superoxide dismutase.

| Time (in hours) | 0–24 | 24–40 | 40–42 | 42–44 |
| --- | --- | --- | --- | --- |
| % of inhibition | 61 | 74 | 72 | 78 |

EXAMPLE 11

2 kilo of weight *Photobacterium leiognathi* were lysed by stirring in 8 liters of cold distilled water for 3 hours at 4° C and then centrifuged at 16 300 g for 10 minutes at 4° C. The residues were dispersed in a Waring blendor in 9 l of water and left at 4° C overnight, then centrifuged as before. To the clear combined supernatants was added KCl to a final concentration of 0.1 M (final pH of 6.5) and the solution was then heated at 58° C for 3 minutes by circulation through a coil at this temperature. The resultant suspension of proteins was cooled to 4° C and clarified by centrifugation at 16 300 g for 5 minutes at 4° C. The supernatant was concentrated to 6 l by ultrafiltration using a fiber filter HIDP10 and was then brought to 25% saturation with ammonium sulfate by dialysis against 2 l of saturated ammonium sulfate. Precipitated material was removed by centrifugation and discarded. The active fraction of superoxide dismutase was precipitated from the supernatant by addition of ammonium sulfate to 75% saturation and this precipitate was dissolved in $5 \times 10^{-2}$M glycine buffer pH 8.6 containing $5 \times 10^{-2}$M NaCl, and dialysed overnight against the same buffer. The one liter of solution was then applied to a column of DEAE-Sephadex A-50 (5.4 × 54 cm) equilibrated with $5 \times 10^{-2}$M glycine, $5 \times 10^{-2}$M NaCl, pH 8.6. Protein was eluted from the column with a linear gradient of $5 \times 10^{-2}$M glycine, $5 \times 10^{-2}$M NaCl to $3 \times 10^{-1}$M glycine, $5 \times 10^{-1}$M NaCl, pH 8.6. The first active fraction of superoxide dismutase (5.7 g, $10.9 \times 10^6$ units) was not retained by the column and appeared in the volume obtained on washing with $5 \times 10^{-2}$M glycine, $5 \times 10^{-2}$M NaCl pH 8.6. The second superoxide dismutase was eluted at $2.0 \times 10^{-2}$ glycine $3.5 \times 10^{-2}$M NaCl, pH 8.6 and was the non-haematinic ferroprotein superoxide dismutase.

Fractions containing the first superoxide dismutase activity were dialyzed against $5 \times 10^{-4}$M phosphate buffer, pH 7.4, fltered through a column of DEAE-cellulose (3.3 × 40 cms) in the same buffer, and then adsorbed onto a column of carboxymethyl cellulose (CM − 52, 3.5 × 32 cm). A linear gradient of phosphate (750 ml each of $5 \times 10^{-1}$M) pH 7.0 was applied. Superoxide dismutase (0.23 g, $6.7 \times 10^6$ units) was eluted at a phosphate concentration of $2.6 \times 10^{-2}$M. The purified dismutase was concentrated and stored as a precipitate in saturated ammonium sulfate solution or maintained frozen at −20°.

Measurements of sedimentation velocity were made with a Beckman Spinco model L 2 − 65 B ultracentrifuge according to the method of Martin and Ames (J. Biol. Chem. 236, 1372–79, 1961) with a linear 5 to 20% (W/V) sucrose gradient. An SW 65 K rotor was used and centrifugation was for 17 hours at 45 000 rpm at 3° with suitable markers. The sedimentation coefficient for superoxide dismutase was 2.7 using as references the following proteins: yeast alcohol dehydrogenase (7.4), horse liver alcohol dehydrogenase (4.82), and cytochrome C (1.45). The molecular weight of native dismutase was calculated to be 33,070.

At the final stage of purification the dismutase gave a single band of protein (and activity) on acrylamide gel electrophoresis carried out according to the procedure of Davis (Ann. N.Y. Acad. Sci., 121, 404–427, 1964). Electrophoresis was performed in 7.5% acrylamide gel with Tris-glycine buffer, pH 8.5 and a constant current of 4 mA per gel. The protein was stained using Coomassie blue in 7% acetic acid destained with 7% acetic acid.

Sodium dodecylsulfate (SDS) — polyacrylamide gel electrophoresis was performed. The samples were incubated at 37° C for 2 hours in $10^{-2}$M phosphate buffer, pH 7.0, 1% in SDS, and 1% β-mercaptoethanol, in the presence of 8 M of urea; 10% acrylamide solutions were used for the preparation of the gels and electrophoresis was carried out for 2 hours at a constant current of 16 mA per gel. Bacteriocuprein gave two bands with Rf values of 0.75 and 0.79 as compared with those obtained for yeast alcohol dehydrogenase 0.41, myoglobin 0.72, lysozyme 0.83 and cytochrome c 0.91. The native enzyme therefore consists of two different subunits of molecular weight 17,000 and 15,500. The isoelectric point was determined on a LKB 8101 electrofocusing column with Ampholine (pH 7 to ) in a sucrose gradient. Bacteriocuprein showed an isoelectric point of 8.25.

The pH dependance of dismutase activity determined either with xanthine oxidase hypoxanthine and luminol, or by inhibition of reduction of cytochrome c showed a maximum at pH 9.

Bacteriocuprein showed high thermal stability; no changes in enzymatic activity were found after incubation for 60 minutes at 20°, 30°, 40° or 50° C at pH 7.8. Incubation for 120 minutes at 60° caused a 58% decrease in the activity whereas the enzyme was completely inactivated after 90 minutes at 70° C. The stability of dismutase activity as a function of pH was determined after a 30 minute preincubation at 20° in buffers ranging from pH 4 to 11. Activity was then studied by the standard test at pH 9.0. Bacteriocuprein was completely stable between pH 5 and 11 but at pH 4.0 lost 65% of the original activity.

Quantitative estimations of copper, zinc and iron were made by atomic absorption analysis using an Instrumentation Laboratories IL 253 Spectrometer. One atom of copper (1.02) and two atoms of zinc (2.5) per molecule of superoxide dismutase were found. Neither manganese or iron could be detected. Calculations were based on protein concentrations determined by the method of fringes using the interference optics of a Spinco Model E ultracentrifuge. The ultraviolet absorption spectrum using a Cary 14 showed that a

TABLE I

Effect of oxygen on superoxide dismutase activities

| | Units | | Ratio of units |
|---|---|---|---|
| | Air | Oxygen | $O_2$/air |
| Total units | 28,220 | 102,480 | 3.63 |
| Bacteriocuprein | 12,920 | 28.880 | 2.23 |
| Ferro/SOD | 15,300 | 73,600 | 4.81 |
| Ratio units of Ferro SOD/cupro SOD | 1.18 | 2.55 | | solution of 1 mg bacteriocuprein ml has an absorption of 0.651 at 280 nm and 0.434 at 260 nm.

Samples (5 gm of wet weight) of *Photobacterium leiognathi* were grown in liquid media with either air or pure oxygen. Each was then dispersed in water (20 ml) and sonicated for 1 minute and then centrifuged. The debris was resuspended in 20 ml of $5 \times 10^{-4}$M phosphate pH 7.4 and resonicated for 2 minutes and again centrifuged. The combined supernatants were adjusted to 0.1 M KCl, heated at 55° for 3 minutes then cooled and centrifuged. Fractionation with ammonium sulfate (33 – 80% saturation cut) by dialysis against appropriate quantities of saturated ammonium sulfate gave crude superoxide dismutase which was separated into bacteriocuprein and the ferroprotein superoxide dismutase on a small column of DEAE-sephadex A-50 using a gradient of $5 \times 10^{-2}$M glycine $5 \times 10^{-2}$M NaCl pH 8.6 to 0.3 M glycine 0.5 M NaCl pH 8.6 (Table 1).

Various modifications of the compositions and method of the invention may be made without departing from the spirit or scope thereof and it is to be understood that the invention is to be limited only as defined in the appended claims.

I claim:

1. A composition protected from autooxidation comprising at least one member of the group consisting of lipids and antioxidants for foodstuffs and an effective amount of a superoxide dismutase of extracted from photobacterium marine bacterial cultures characterized by having a molecular weight of about 40,000 ± 2500, a pHi point of about 4 to 7, containing 1 to 2 atoms of non-hematinic iron per mole of superoxide dismutase and having a maximum enzymatic activity at a pH between 8.5 to 10.

2. The composition of claim 1 wherein the antioxidant is selected from the group consisting of pyrogallol and ascorbic acid.

3. A composition protected from autooxidation comprising at least one member of the group consisting of lipids and antioxidants for foodstuffs and an effective amount of a superoxide dismutase extracted from photobacterium marine bacterial cultures characterized by a molecular weight of 33,000 ± 2500, a pHi point of about 8.25, having a maximum enzymatic activity at a pH of 8.5 to 10 and containing about 1 atom of copper and about 2.0 atoms of zinc per mole of superoxide dismutase.

4. The composition of claim 18 wherein the antioxidant is selected from the group consisting of pyrogallol and ascorbic acid.

5. A method of protecting lipids and antioxidnts for foodstuffs from oxidation comprising incorporating into lipids and antioxidants for foodstuffs an effective amount of a superoxide dismutase of extracted from photobacterium marine bacterial cultures characterized by having a molecular weight of about 40,000 ± 2500, a pHi point of about 4 to 7, containing 1 to 2 atoms of non-hermatinic iron per mol of superoxide dismutase and having a maximum enzymatic activity at a pH between 8.5 to 10.

6. A method of protecting lipids and antioxidants for foodstuffs from oxidation comprising incorporating into lipids and antioxidants for foodstuffs an effective amount of a superoxide dismutase extracted from photobacterium marine bacterial cultures characterized by a molecular weight of 33,000 ± 2500, pHi point of about 8.25, having a maximum enzymatic activity at a pH of 8.5 to 10 and containing about 1 atom of copper and about 2.0 atoms of zinc per mole of superoxie dismutase.

* * * * *